United States Patent [19]

Shiroto et al.

[11] Patent Number: 4,992,622
[45] Date of Patent: Feb. 12, 1991

[54] METHOD OF SEPARATING 2,6-DIISOPROPYLNAPHTHALENE FROM A MIXTURE CONTAINING DIISOPROPYLNAPHTHALENE ISOMERS

[75] Inventors: Yoshimi Shiroto; Mitsunori Shimura; Kenji Shimokawa, all of Yokohama; Yoshio Fukui, Tokyo; Yakudo Tachibana, Kasukabe; Kazuhiko Tate, Yokohama; Hiroaki Taniguchi, Kuki, all of Japan

[73] Assignees: Chiyoda Corporation; NKK Corporation, both of Japan

[21] Appl. No.: 388,590

[22] Filed: Aug. 2, 1989

[30] Foreign Application Priority Data

Dec. 26, 1988 [JP] Japan .................. 63-328473
Dec. 26, 1988 [JP] Japan .................. 63-328474
Dec. 26, 1988 [JP] Japan .................. 63-328475

[51] Int. Cl.$^5$ .................................. C07C 7/13
[52] U.S. Cl. ......................... 585/828; 208/310 Z
[58] Field of Search ............. 208/310 Z; 585/820, 585/826, 827, 828

[56] References Cited

U.S. PATENT DOCUMENTS

| 2,985,589 | 5/1961 | Broughton | 585/825 |
| 3,306,945 | 2/1967 | Conviser | 585/829 |
| 3,392,113 | 2/1968 | Rosset | 585/826 |
| 3,668,267 | 6/1972 | Hedge | 208/310 Z |
| 3,895,080 | 7/1975 | Davis | 208/310 Z |
| 4,014,949 | 3/1977 | Hedge | 208/310 Z |
| 4,029,717 | 6/1977 | Healy et al. | 585/828 |

FOREIGN PATENT DOCUMENTS 2199590 7/1988 United Kingdom ............... 585/804

Primary Examiner—Curtis R. Davis
Assistant Examiner—William C. Dienler
Attorney, Agent, or Firm—Lorusso & Loud

[57] ABSTRACT

A method of separating 2,6-diisopropylnaphthalene from a mixture containing 2,6-diisopropylnaphthalene and structural isomers thereof including the 2,7-isomer is disclosed, wherein the mixture is first subjected to a selective adsorption and desorption treatment using a zeolite absorbent capable of adsorbing the 2,7-isomer to obtain a first extract containing the sorbed 2,7-isomer and a first raffinate containing non-sorbed isomers including the 2,6-isomer, the 2,6-isomer being thereafter separated from the first raffinate.

16 Claims, 2 Drawing Sheets

METHOD OF SEPARATING 2,6-DIISOPROPYLNAPHTHALENE FROM A MIXTURE CONTAINING DIISOPROPYLNAPHTHALENE ISOMERS

BACKGROUND OF THE INVENTION

This invention relates to a method of separating 2,6-diisopropylnaphthalene from a mixture containing 2,6-diisopropylnaphthalene and its structural isomers.

2,6-Diisopropylnaphthalene (hereinafter referred to as 2,6-isomer) which is an important raw material for the production of polyesters can be obtained by reaction of naphthalene with propylene. Since the reaction produces a number of diisopropylnaphthalenes such as 1,3-, 1,7-, 1,4-, 2,6-, 2,7- and 1,6-isomers, it is necessary to separate the 2,6-isomer from the isomeric mixture. No effective, industrially applicable methods are, however, known for the separation of the 2,6-isomer.

SUMMARY OF THE INVENTION

It is, therefore, an object of the present invention to provide a method which can effectively separate 2,6-isomer from a mixture containing 2,6- and other isomers with a high separation efficiency.

Another object of the present invention is to provide a method by which not only 2,6-isomer but also 2,7-isomer can be separated.

In accomplishing the foregoing objects, there is provided in accordance with the present invention a method of separating 2,6-diisopropylnaphthalene from a mixture containing 2,6-diisopropylnaphthalene and structural isomers thereof including a 2,7-isomer, comprising the steps of:

(a) subjecting said mixture to a selective adsorption and desorption treatment using a first zeolite absorbent capable of adsorbing the 2,7-isomer to obtain a first extract containing the sorbed 2,7-isomer and a first raffinate containing non-sorbed isomers including the 2,6-isomer; and (b) separating the 2,6-isomer from said first raffinate.

In one embodiment, the first zeolite absorbent is capable of selectively adsorbing both 1,7- and 2,7- isomers so that the 1,7- and 2,7-isomers are removed from the mixture as the first extract, and step (b) comprises subjecting the first raffinate to a selective adsorption and desorption treatment using a second zeolite absorbent capable of adsorbing the 2,6-isomer to remove the 2,6-isomer therefrom as an extract and to obtain a second raffinate containing non-sorbed isomers.

In another embodiment, before step (a) the mixture is subjected to a distillation treatment to separate the 1,3- and 1,7-isomers therefrom, the resulting mixture form which the 1,3- and 1,7-isomers have been removed being subjected to step (a).

BRIEF DESCRIPTION OF THE DRAWINGS

Other objects, features and advantages of the present invention will become apparent from the detailed description of the invention which follows, when considered in light of the accompanying drawings, in which.

DETAILED DESCRIPTION OF THE INVENTION

Figure 1:
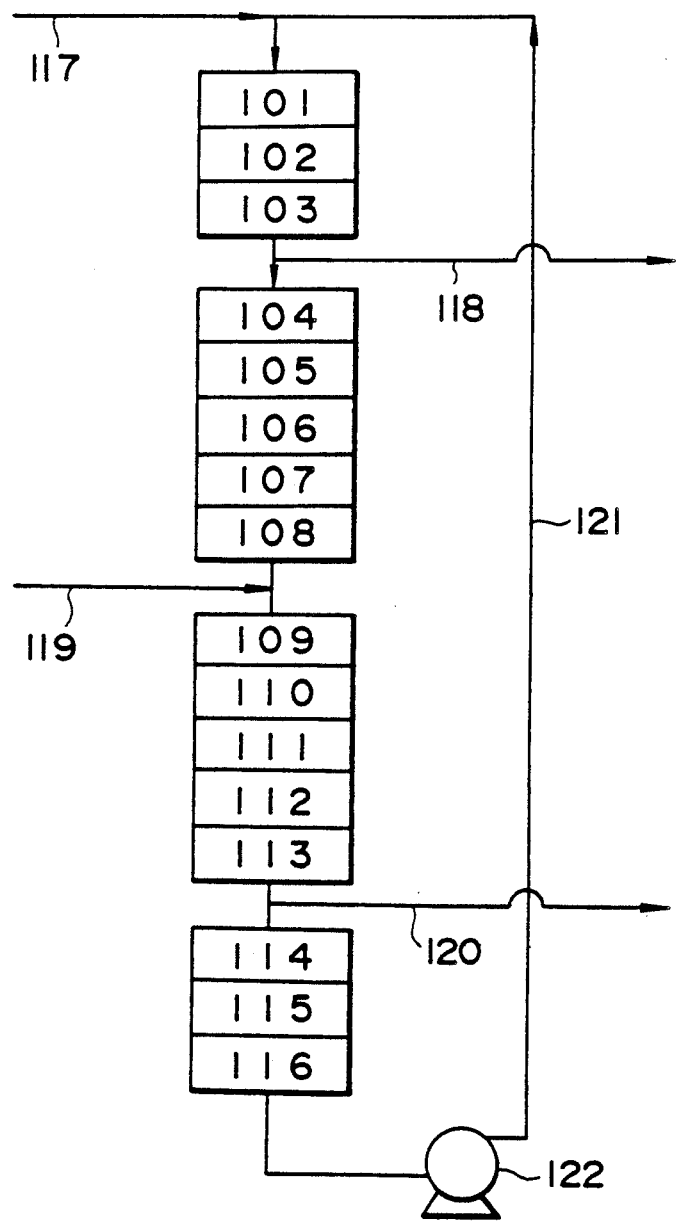
FIG. 1 is a schematic illustration embodying the principle of a simulated, countercurrent moving bed system used in the method of the present invention.

In the method of the present invention, a mixture containing 2,6-diisopropylnaphthalene and structural isomers thereof including a 2,7-isomer is subjected to a selective adsorption and desorption treatment (step (a)) using a first zeolite absorbent capable of adsorbing the 2,7-isomer to obtain a first extract containing the sorbed 2,7-isomer and a first raffinate containing non-sorbed isomers including the 2,6-isomer, the 2,6-isomer being subsequently recovered from the first raffinate (step (b)).

In one preferred embodiment, the first zeolite absorbent is capable of selectively adsorbing both 1,7- and 2,7-isomers so that the 1,7- and 2,7-isomers are removed from said mixture as the first extract, and the recovery of the 2,6-isomer from the first raffinate (step (b)) is effected by subjecting the first raffinate to a selective adsorption and desorption treatment using a second zeolite absorbent capable of adsorbing the 2,6-isomer to remove the 2,6-isomer therefrom as an extract and to obtain a second raffinate containing non-sorbed isomers. The first extract may be subjected to a distillation treatment to separate the 1,7- and 2,7-isomers from each other, as desired.

Each of the first and second zeolite absorbents is preferably an X-type or Y-type, Faujasite zeolite having a $SiO_2/Al_2O_3$ molar ratio of 2–6. The first zeolite absorbent is preferably a zeolite of the above-mentioned type having at least 80 mole %, more preferably at least 90 mole % of its exchangeable cations ion-exchanged with at least one cation selected from the group consisting of Li, Na, K, Ba and Pb ions. Especially preferred is an Y-type zeolite ion-exchanged with K and/or Li ions. The second zeolite absorbent is preferably a zeolite of the above-mentioned type having at least 80 mole % of its exchangeable cations ion-exchanged with at least one cation selected from the group consisting of Na, Pb and Ba. Especially preferred is an Y-type zeolite ion-exchanged with Na and/or Pb ions. The use of a zeolite absorbent containing proton is not recommendable because it can act as a transalkylation catalyst of the di-isomers so that the yield of the 2,6-isomer is lowered.

The first and second zeolite absorbent preferably have a particle size of 3–300 mesh (Tyler). It is preferred that each of the first and second zeolite absorbents have a moisture content of 5% by weight or less, more preferably 3% by weight or less, when measured in terms of ignition loss at 1000° C., for reasons of improved adsorption selectivity and efficiency. Moisture contained in the zeolite absorbent is located in the cationic active site or within pores thereof, so that the weight of a substance adsorbed per unit weight of the absorbent is decreased.

The selective adsorption and desorption treatment in each of steps (a) and (b) is preferably performed at a temperature of about 50°–300° C., more preferably about 80°–200° C. and such a pressure that a mixture to be treated is present in a liquid state and may be effected by a method including the steps of:

(i) contacting a mixture to be treated with the zeolite absorbent contained in an adsorption zone and maintained at adsorption conditions to effect selective adsorption of a target isomer contained in the mixture;

(ii) withdrawing a raffinate containing non-sorbed isomers from the adsorption zone;

(iii) contacting the zeolite absorbent carrying the sorbed, target isomer and maintained at desorption conditions with a desorbent material to effect removal of the target isomer therefrom; and (iv) withdrawing from the zeolite absorbent an extract containing the removed target isomer.

As the desorbent material may be used a substance capable of being quickly adsorbed by the absorbent material for replacement for the sorbed target isomer. An aromatic desorbent material, especially an alkylbenzene of the formula:

$(R')_n\text{-Ph-R}$ wherein Ph represents a benzene nucleus, R and R' represent independently from each other a methyl, an ethyl, an n-propyl or an isopropyl, and n is an integer of 0 or 1, is suitably used.

The above adsorption and desorption treatment is advantageously carried out using a simulated, countercurrent moving bed system. By this, there is obtainable 2,6-isomer having a purity of as high as 99% or more. Such a moving bed system per se is known in the art and is applied for selective removal of a specific xylylene compound from its isomers (Japanese Examined Publication (Tokkyo Kokoku) No. 42-15681 and No. 50-10547).

One example of such a simulated countercurrent moving bed system is shown in FIG. 1. The system includes a fixed bed of a said first zeolite absorbent containing at least four serially interconnected zones (16 zones in the specifically illustrated case) having fluid flow connecting means between adjacent zones and between the outlet of the last zone and the inlet of the first zone in the series, to thereby provide cyclic, fluid flow. Designated as 122 is a pump for causing the fluid flow in the direction shown by the arrow. The number of the interconnected zones are not specifically limited.

In the system, four different operations, i.e. adsorption of a target isomer, concentration of the adsorbed target isomer, desorption of the adsorbed target isomer using a desorbing material, and recovery of the desorbing material are being simultaneously carried out in the respective zones.

In the illustrated stage, the zones 101-103 are performing the desorption, the zones 104-108 are performing the concentration, the zones 109-113 are performing the adsorption and the zones 114-116 are performing the recovery. That is, a mixture to be treated is introduced through a line 119 into one, sorbing zone 109 and then into succeeding zones 110-113 to selectively sorb the target isomer contained in the mixture.

The desorbent material is fed through a line 117 to a desorbing zone 101 and is passed through the zones 102 and 103 to remove the adsorbed target isomer. The desorbing zone 101-103 are positioned upstream of the adsorbing zones 109-113 such that intermediate, concentrating zones 104-108 are defined between the adsorbing zones 109-113 and desorbing zones 101-103 and that recovering zone 114-116 are defined downstream of the adsorbing zone 109-112.

At the same time, the mixture from which the target isomer has been removed by adsorption and which contains non-sorbed isomers is withdrawn from the fluid flow connecting means extending between the adsorbing zone 113 and the recovering zone 114 through a line 120 as a raffinate. Further, the removed target isomer is simultaneously withdrawn from the fluid flow connecting means extending between the desorbing zone 103 and the concentrating zone 104 through a line 118 as an extract.

A portion of the removed target isomer is fed from the desorbing zone 103 to the concentrating zones 104-108 and is replaced for the sorbed isomers other than the target isomer on the absorbent. The absorbent which has sorbed the desorbent material is contacted in the recovery zones 114-116 with a portion of non-sorbed isomers for replacement therewith. The thus recovered desorbent material is fed to the desorbing zones 101-103.

The point of introducing the mixture to be treated is periodically advanced downstream, while simultaneously and equally advancing the points of introducing the desorbent material and of withdrawing the raffinate and the extract. Therefore, in the next stage succeeding the illustrated stage, the desorption, concentration, adsorption and recovery are effected in the zones 102-104, 105-109, 110-114 and 115-101. Thus, though the bed of the absorbent is fixed in the treatment tower, there is established a system similar to a countercurrent moving bed by periodically advancing the introduction and withdrawing points downstream with respect to the fluid flow.

In the above-described first embodiment involving the two stage adsorption and desorption treatment, the first raffinate obtained in the first stage can be fed to the second stage as such or after removing the desorbent material contained therein. When 2,6-isomer is separated from the isomeric mixture by a one-stage adsorption and desorption treatment, it is necessary to select a specific absorbent and to use an absorbing tower having a large number of absorption steps and a large amount of absorbent. In contrast, the use of the two stage treatment in accordance with the present invention, the absorbent can be selected without difficulty and the process can be performed at a high speed without using an adsorption column with a relatively small number of steps.

The adsorptivity of diisopropylnaphthalenes on a zeolite absorbent relative to the 2,6-isomer may be expressed by a relative separation factor $\beta(2,6/i)$ defined by the following formula:

$$\beta(2,6/i) = K(2,6)/K(i)$$

wherein K(2,6) and K(i) represent solid/liquid equilibrium constants of the 2,6-isomer and an isomer "i", respectively, defined as follows:

$$K(2,6) = \frac{\text{Concentration (g/cc) of 2,6-isomer in adsorption phase}}{\text{Concentration (g/cc) of 2,6-isomer in liquid phase}}$$

$$K(i) = \frac{\text{Concentration (g/cc) of isomer "i" in adsorption phase}}{\text{Concentration (g/cc) of isomer "i" in liquid phase}}$$

An isomer whose $\beta(2,6/i)$ is smaller than 1 is more absorptive than the 2,6-isomer. Conversely, an isomer whose factor $\beta(2,6/i)$ is greater than 1 is more difficult to be adsorbed in comparison with the 2,6-isomer. An absorbent which provides factors $\beta(2,6/1,7)$ and $\beta(2,6/2,7)$ of less than 1 (preferably 0.7 or less, more preferably 0.5 or less) is suitably used as an absorbent selectively adsorbing the 1,7- and 2,7-isomers. An absorbent which provides $\beta(2,6/i)$ of greater than 1 (where i is other than 1,7 and 2,7) may be used as an absorbent selectively adsorbing 2,6-isomer and other isomers than 1,7- and 2,7- isomers. As an absorbent to be used for selectively adsorbing the 2,6-isomer, it is preferable to use one which provides the factor $\beta(2,6/i)$ of 1.5 or more, more preferably 2 or more.

Figure 2:
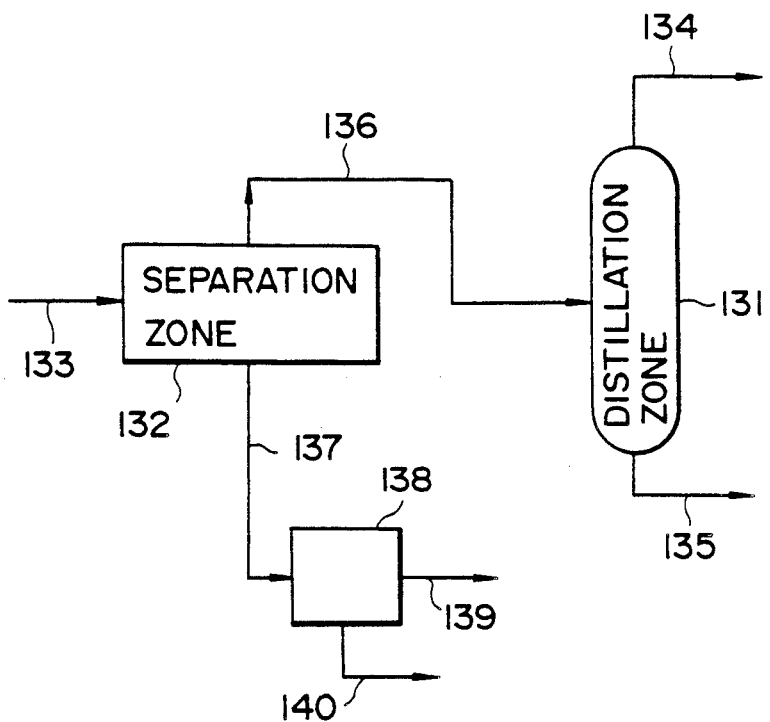
FIG. 2 is a flow diagram showing one embodiment of the present invention.

FIG. 2 shows a second embodiment according to the present invention, in which the isomeric mixture from a line 133 is subjected to an adsorption and desorption treatment in a zone 132 containing an absorbent capable of adsorbing 2,7- and 1,7-isomers, thereby to obtain an extract containing the 2,7- and 1,7-isomers through a line 136 and a raffinate through a line 137. The extract is then introduced into a distillation zone 131 to separate the extract into the 1,7-isomer as a distillation top through a line 134 and the 2,7-isomer as a bottom product through a line 135. The raffinate is fed to a separation zone 138 to isolate the 2,6-isomer through a line 139. The other isomers are recovered through a line 140.

Figure 3:
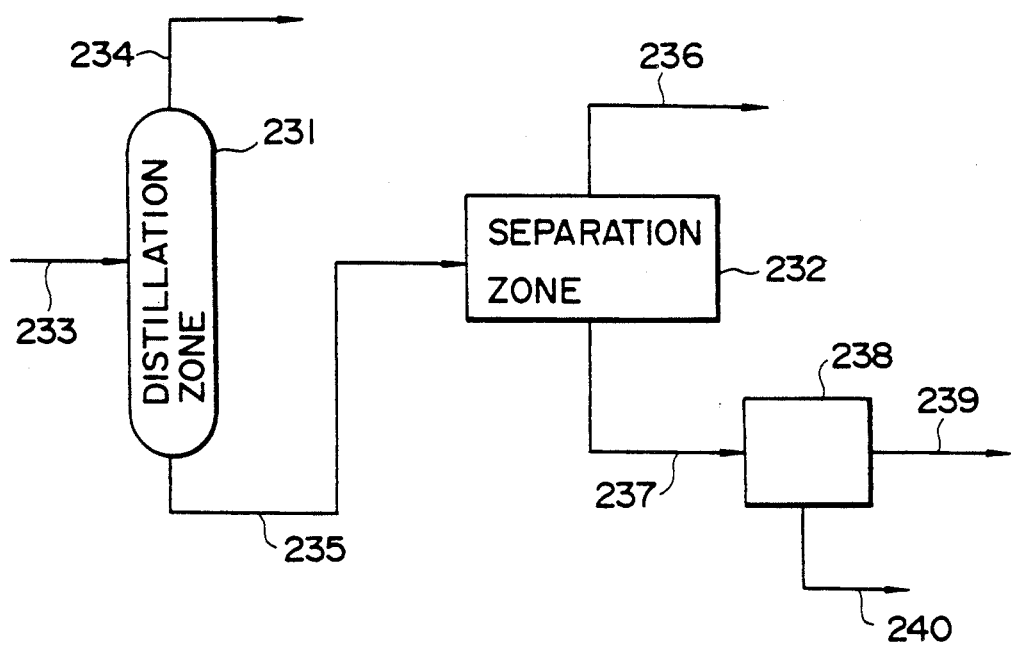
FIG. 3 is a flow diagram showing another embodiment of the present invention.

FIG. 3 shows a third embodiment according to the present invention, in which the isomeric mixture from a line 233 is first introduced into a distillation zone 231 to separate the 1,3- and 1,7-isomers therefrom through a line 234. The resulting mixture from which the 1,3- and 1,7-isomers have been removed is fed through a line 235 to a selective adsorption and desorption treatment zone 232, preferably of a simulated, countercurrent moving bed system as described above, containing an absorbent capable of adsorbing the 2,7-isomer, thereby to obtain a first extract containing the sorbed 2,7-isomer (line 236) and a first raffinate containing non-sorbed isomers including the 2,6-isomer. The 2,6-isomer is then fed through a line 237 to a separation zone 238 to isolate the 2,6-isomer through a line 239. The other isomers are recovered through a line 240.

As separation method in the separation zone 138 or 238, there may be adopted a precipitation method (disclosed, for example, in Japanese Published Unexamined patent application (Tokkyo Kokai) No. 62-226931), an inclusion method (disclosed, for example, in Tokkyo Kokai No. 63-88141) or an adsorption and desorption method such as described above.

The adsorption and desorption treatment in the zone 132 or 232 is preferably carried out by using a simulated, countercurrent moving bed system as described above. For the reasons as set forth below, the desorbing, concentrating, sorbing and recovering zones are preferably operated under conditions satisfying the following conditions:

| desorbing zone: | L(I)/S(I) > 0.2 + L(IV)/S(I) |
| concentrating zone: | L(II)/S(II) > 0.1 + L(IV)/S(II) |
| sorbing zone: | L(III)/S(III) < 0.3 + L(IV)/S(III) |
| recovering zone: | 0.8 < L(IV)/S(IV) < 1.0 | wherein L(I) through L(IV) represent the flow rates, in terms of cc/hour, of liquids flowing through the desorbing zone, concentrating zone, sorbing zone and recovering zone, respectively, and S(I) through S(IV) represent the simulate moving rates, in terms of cc/hour, of the solid absorbent through the desorbing zone, concentrating zone, sorbing zone and recovering zone, respectively.

In the desorbing zone, the absorbent which has sorbed a high concentration of the 2,7-isomer (or both 2,7- and 1,7-isomers) is contacted with the desorbent material. If the liquid flow rate in this zone is too low to sufficiently desorb the 2,7-isomer, the 2,7-isomer contaminates the raffinate, resulting in the recovery rate of the 2,7-isomer. More preferably, the desorbing zone is operated under the following condition:

$$L(I)/S(I) > 0.25 + L(IV)/S(I)$$

In the concentrating zone, the isomers other than the 2,7-isomer (or 1,7- and 2,7-isomers) which have been sorbed by the absorbent are perfectly desorbed. If the liquid flow rate in this zone is too low to sufficiently desorb the isomers other than the 2,7-isomer, they contaminate the extract, resulting in the purity of the 2,7-isomer extract product. More preferred condition is as follows:

$$L(II)/S(II) > 0.15 + L(IV)/S(II)$$

In the adsorption zone, the 2,7-isomer (or 1,7- and 2,7-isomers) contained in the isomeric mixture is sorbed by the absorbent while the other isomers are recovered as a raffinate together with the desorbent material. If the liquid flow rate is so high that the 2,7-isomer is failed to be sufficiently sorbed by the absorbent, the 2,7-isomer is discharged from the absorption zone and is incorporated into the raffinate, resulting in the lowering of the 2,7-isomer recovery rate. More preferred condition is as follows:

$$L(III)/S(III) < 0.25 + L(IV)/S(III)$$

In the recovery zone, di-isomers from which the 2,7-isomer have been removed in the adsorption zone are adsorbed by the absorbent. The absorbent carrying the di-isomers is fed to the adsorption zone where the di-isomers are replaced by more adsorptive 2,7-isomer and are recovered as the raffinate, as described above. The liquid flow discharged from the bottom of the recovery zone consists essentially of the desorbent material and no longer contains any di-isomers. The thus recovered desorbent material is then fed to the desorption zone. If the liquid flow rate is too high to sufficiently adsorb less adsorptive di-isomers, the di-isomers contaminates the desorbent material and, therefore, the extract, resulting in the lowering of the purity of the 2,7-isomer extract product. If, on the other hand, the liquid flow rate is excessively low, there is a danger that the di-isomers other than the 2,7-isomer are carried by the adsorbent and are passed successively to the adsorption zone, concentration zone and the desorption zone, thereby to contaminate the extract. More preferred condition is as follows:

$$0.8 < L(IV)/S(IV) < 0.95$$

The adsorptivity of diisopropylnaphthalenes on a zeolite absorbent relative to the 2,7-isomer may be expressed by a relative separation factor $\beta(2,7/i)$ defined by the following formula:

$$\beta(2,7/i) = K(2,7)/K(i)$$

wherein $K(2,7)$ and $K(i)$ represent solid/liquid equilibrium constants of the 2,7-isomer and an isomer "i", respectively, defined as follows:

$$K(2,7) = \frac{\text{Concentration (g/cc) of 2,7-isomer in adsorption phase}}{\text{Concentration (g/cc) of 2,7-isomer in liquid phase}}$$

$$K(i) = \frac{\text{Concentration (g/cc) of isomer "}i\text{" in adsorption phase}}{\text{Concentration (g/cc) of isomer "}i\text{" in liquid phase}}$$

An isomer whose $\beta(2,7/i)$ is smaller than 1 is more absorptive than the 2,7-isomer. Conversely, an isomer whose factor $\beta(2,7/i)$ is greater than 1 is more difficult to be adsorbed in comparison with the 2,7-isomer. The factor $\beta(2,7/1,7)$ of the 1,7-isomer for a zeolite absorbent is about 1, while those of the other isomers are greater than 1. Therefore, the 2,7- and 1,7-isomers can be separated from the other isomers by selective adsorption with the zeolite absorbent. It is preferable to use a zeolite absorbent providing the factor $\beta(2,7/i)$ of more than 2 for the isomers other than the 1,7- and 2,7 isomers. Further, it is preferable to use a desorbent material whose relative separation factor $\beta(2,7/D)$ is in the range of 0.5–3, more preferably 1–2 from the standpoint of economy. If the factor $\beta(2,7/D)$ becomes large in excess of 3, it is necessary to use a large amount of the desorbent material. On the other hand, a desorbent material whose factor $\beta(2,7/D)$ is smaller than 0.5 requires a large amount of the absorbent.

The following examples will further illustrate the present invention.

EXAMPLE 1

Naphthalene was isopropylated and the product was separated by distillation to obtain an isomeric mixture containing diisopropylnaphthalenes. The isomeric mixture had the composition shown in Table 1 below.

TABLE 1

| Component | Content (% by weight) |
| --- | --- |
| 2,6-isomer | 18.7 |
| 2,7-isomer | 15.6 |
| 1,6-isomer | 13.8 |
| 1,7-isomer | 17.3 |
| 1,3-isomer | 20.7 |
| 1,4-isomer | 7.2 |
| other isomers | 5.3 |
| components other than diisopropylnaphthalenes | 1.4 |

The isomeric mixture was then subjected to adsorption treatments using each of the four Y-zeolite absorbents obtained in the following manner.

About 10 g of a sodium-type Y-zeolite ($SiO_2/Al_2O_3$ molar ratio: 4.6, particle size: 40–80 mesh) were mixed with about 100 g of a 0.5 mol/liter aqueous solution of a metal chloride and the mixture was allowed to stand at 90°–100° C. for 2 hours for effecting ion-exchange with the metal. After filtration, the precipitate was mixed again with the above aqueous solution and the mixture was heat-treated in the same manner. The above procedures were repeated once more and the precipitate was dried and calcined at 400° C. for 3 hours to obtain an absorbent ion-exchanged with K (Absorbent No. 1) Na (Absorbent No. 2), Li (Absorbent No. 3), Ba (Absorbent No. 4) or Pb (Absorbent No. 5).

The adsorption treatment was carried out as follows: Into a 30 cc autoclave, about 4 g of the absorbent, about 6.5 g of the above mixture having the composition shown in Table 1 and about 1.5 g of diethylbenzene (desorbent material) were added and the mixture was stirred for 120 minutes at a constant temperature. The resulting mixture was filtered. The absorbent was washed with isooctane and then subjected to extraction with toluene by means of a Soxhlet extractor. The filtrate and the extracted material were each analyzed by gas chromatography, from the results of which relative separation factors (2,6/i) were calculated. The results are shown in Table 2.

TABLE 2

| Absorbent | Ion Exchanged Metal | Relative Separation Factor $\beta$ | | | | |
| --- | --- | --- | --- | --- | --- | --- |
| | | (2,6/2,7) | (2,6/1,7) | (2,6/1,6) | (2,6/1,3) | (2,6/1,4) |
| No. 1 | K | 0.07 | 0.06 | 0.5 | 3.3 | 1.3 |
| No. 2 | Na | 1.4 | 0.7 | 2.0 | 10.0 | 5.0 |
| No. 3 | Li | 0.5 | 0.4 | 0.7 | 2.5 | 2.7 |
| No. 4 | Ba | 0.8 | 0.7 | 2.5 | 10.0 | 10.0 |
| No. 5 | Pb | 1.4 | 0.8 | 2.0 | 10.0 | 10.0 |

From the results shown in Table 2, it will be appreciated that Adsorbents Nos. 1 (K) and 3 (Li), which have a separation factor of smaller than 1 are suited for use as an adsorbent capable of selectively adsorbing 1,7- and 2,7-isomers, Absorbents Nos. 2, 4 and 5 are suited for use as an absorbent capable of selectively adsorbing 2,6-isomer.

EXAMPLE 2

A zeolite having a $SiO_2/Al_2O_3$ molar ratio shown in Table 3 was ion-exchanged with Ba ion in the same manner as that in Example 1. Using the resulting absorbent, the isomeric mixture of Table 1 was subjected to an adsorption treatment in the same manner as that in Example 1. The amount of the adsorbed material (W) per unit amount of the absorbent was as summarized in Table 3.

TABLE 3

| Experiment No. | Zeolite | | W (g/g) |
| --- | --- | --- | --- |
| | Type | $SiO_2/Al_2O_3$ | |
| 1 | X | 2.50 | 0.07 |
| 2 | Y | 4.60 | 0.11 |
| 3 | Y | 5.60 | 0.17 |
| 4 | L | 6.10 | 0.03 |

From the results shown in Table 3, it is appreciated that a zeolite absorbent having a $SiO_2/Al_2O_3$ molar ratio of above 6 fails to provide satisfactory adsorptivity.

EXAMPLE 3

Absorbent No. 4 shown in Table 2 was treated so as to vary its water content as shown in Table 4. The isomeric mixture shown in Table 1 was subjected to an adsorption treatment using the resulting Absorbent No. 4 in the same manner as that in Example 1. The amount of the adsorbed material (W) per unit amount of the absorbent was as summarized in Table 4.

TABLE 4

| Experiment No. | Water content (wt %) | W (g/g) |
| --- | --- | --- |
| 1 | 0 | 0.12 |
| 2 | 1.0 | 0.11 |
| 3 | 3.0 | 0.10 |
| 4 | 4.2 | 0.08 |
| 5 | 6.0 | 0.06 |

The above results show that the presence of water undesirably reduces the absorptivity.

EXAMPLE 4

The isomeric mixture shown in Table 1 was mixed with 4 times the weight of a desorbent material shown in Table 5. The resulting mixture was subjected to an adsorption treatment in the same manner as that in Example 1 using Absorbent No. 1 shown in Table 2. The separation factor (2,6/i) was calculated to give the results summarized in Table 5.

TABLE 5

| Desorbent material | Relative Separation Factor $\beta$ | | | | | |
|---|---|---|---|---|---|---|
| | (2,6/ 2,7) | (2,6/ 1,7) | (2,6/ 1,6) | (2,6/ 1,4) | (2,6/ 1,3) | (2,6/ D) |
| p-Diisopropyl-benzene | 0.1 | 0.03 | 0.6 | 0.1 | 1.0 | 0.5 |
| Diethylbenzene | 0.09 | 0.09 | 0.5 | 0.2 | 1.2 | 0.1 |
| p-Cymene | 0.08 | 0.1 | 0.6 | 0.3 | 1.2 | 0.1 |
| Cumene | 0.08 | 0.1 | 0.4 | 0.8 | 0.4 | 0.4 |
| Ethylbenzene | 0.08 | 0.09 | 0.3 | 0.6 | 0.4 | 0.7 |
| p-Xylene | 0.09 | 0.1 | 0.5 | 0.3 | 3.3 | 10.0 |
| m-Xylene | 0.04 | 0.1 | 0.5 | 0.2 | 0.4 | 1.7 |
| Toluene | 0.1 | 0.05 | 0.4 | 0.7 | 0.5 | 1.7 |

From the results shown above, it will be appreciated that diethylbenzene and p-cymene which provide $\beta(2,6/2,7)$ and $\beta(2,6/1,7)$ similar to $\beta(2,6/D)$ are suited as an absorbent for the 1,7 and 2,7 isomers.

EXAMPLE 5

The isomeric mixture shown in Table 1 was mixed with 4 times the weight of a desorbent material shown in Table 6. The resulting mixture was subjected to an adsorption treatment in the same manner as that in Example 1 using Absorbent No. 5 shown in Table 2. The separation factor $\beta(2,6i)$ was calculated to give the results summarized in Table 6.

TABLE 6

| Desorbent material | Relative Separation Factor $\beta$ | | | | | |
|---|---|---|---|---|---|---|
| | (2,6/ 2,7) | (2,6/ 1,7) | (2,6/ 1,6) | (2,6/ 1,4) | (2,6/ 1,3) | (2,6/ D) |
| p-Diisopropyl-benzene | 2.0 | 0.6 | 2.0 | 5.0 | 10.0 | 3.3 |
| Diethylbenzene | 1.7 | 0.4 | 2.5 | 3.3 | 10.0 | 1.0 |
| p-Cymene | 0.8 | 0.2 | 1.7 | 2.0 | 10.0 | 0.5 |
| Cumene | 0.6 | 0.2 | 1.3 | 5.0 | 10.0 | 2.0 |
| Ethylbenzene | 0.7 | 0.1 | 1.7 | 2.0 | 10.0 | 1.0 |
| p-Xylene | 0.9 | 0.6 | 1.3 | 3.3 | 10.0 | 1.7 |
| m-Xylene | 0.8 | 1.1 | 1.3 | 5.0 | 10.0 | 2.0 |
| Toluene | 0.8 | 0.4 | 1.0 | 10.0 | 10.0 | 1.0 |

From the results shown above, it will be appreciated that diethylbenzene, ethylbenzene and p-cymene are suited as an absorbent for the 2,6-isomer.

EXAMPLE 6

The isomeric mixture shown in Table 1 was mixed with 4 times the weight of a desorbent material shown in Table 7. The resulting mixture was subjected to an adsorption treatment in the same manner as that in Example 1 using Absorbent No. 2 shown in Table 2. The separation factor $\beta(2,6/i)$ was calculated to give the results summarized in Table 7.

TABLE 7

| Desorbent material | Relative Separation Factor $\beta$ | | | | | |
|---|---|---|---|---|---|---|
| | (2,6/ 2,7) | (2,6/ 1,7) | (2,6/ 1,6) | (2,6/ 1,4) | (2,6/ 1,3) | (2,6/ D) |
| p-Diisopropyl-benzene | 1.1 | 0.2 | 1.4 | 0.6 | 3.3 | 2.5 |
| Diethylbenzene | 2.5 | 1.1 | 3.3 | 5.0 | 10.0 | 1.0 |
| p-Cymene | 0.1 | 0.2 | 0.6 | 1.0 | 1.0 | 0.06 |
| Cumene | 5.2 | 0.3 | 0.7 | 1.0 | 3.3 | 1.4 |
| Ethylbenzene | 0.2 | 0.4 | 0.7 | 10.0 | 3.3 | 0.2 |
| p-Xylene | 0.7 | 0.6 | 1.0 | 10.0 | 1.4 | 0.04 |
| m-Xylene | 0.7 | 0.8 | 1.3 | 10.0 | 10.0 | 0.01 |

TABLE 7-continued

| Desorbent material | Relative Separation Factor $\beta$ | | | | | |
|---|---|---|---|---|---|---|
| | (2,6/ 2,7) | (2,6/ 1,7) | (2,6/ 1,6) | (2,6/ 1,4) | (2,6/ 1,3) | (2,6/ D) |
| Toluene | 0.2 | 0.4 | 0.4 | 10.0 | 2.0 | 0.4 |

From the results shown above, it will be appreciated that diethylbenzene is suited as an absorbent for the 2,6-isomer.

EXAMPLE 7

The isomeric mixture having the composition shown in Table 1 was subjected to a two stage adsorption and desorption separation treatment for the removal of 2,6-isomer using a simulated, countercurrent moving bed system as shown in FIG. 1.

In the first stage, Absorbent No. 1 shown in Table 2 was packed in 12 column chambers No. 101–106, 109–112 and 114–115 (Chambers Nos. 107 and 108 of the concentration zone, No. 113 of the adsorption zone and No. 116 of the recovery zone in FIG. 1 were omitted) each having an inside volume of 70 ml. In the first step, the isomeric mixture was fed at a feed rate of 70 ml/hr through the line 119, a desorbent material (diethylbenzene) at a feed rate of 190 ml/hr through the line 117, while simultaneously discharging an extract through the line 118 at a rate of 180 ml/hr and a raffinate through the line 120 at a rate of 80 ml. The points of the feeding and discharging were shifted downward from one chamber to the adjacent downstream chamber with an interval of 270 seconds. The adsorption was performed at a temperature of 160° C. and a pressure of 10 kg/cm². The 2,6-isomer was recovered as a raffinate with a purity of 55 wt % (desorbent free basis) and recovery rate of 98 wt %.

In the second stage, Absorbent No. 2 shown in Table 2 was packed in 12 column chambers No. 101–106, 109–112 and 114–115 (Chambers Nos. 107 and 108 of the concentration zone, No. 113 of the adsorption zone and No. 116 of the recovery zone in FIG. 1 were omitted) each having an inside volume of 70 ml. In the first step, the raffinate obtained in the first stage was fed at a feed rate of 25 ml/hr through the line 119, a desorbent material (diethylbenzene) at a feed rate of 80 ml/hr through the line 117, while simultaneously discharging an extract through the line 118 at a rate of 70 ml/hr and a raffinate through the line 120 at a rate of 35 ml. The points of the feeding and discharging were shifted downward from one chamber to the adjacent downstream chamber with an interval of 480 seconds. The adsorption was performed at a temperature of 160° C. and a pressure of 10 kg/cm2. The 2,6-isomer was recovered as an extract with a purity of 99 wt % (desorbent free basis) and recovery rate of 90 wt %.

EXAMPLE 8

(a) Separation of 1,3- and 1,7-isomers by Distillation:
A isomeric mixture (about 1.5 liters) obtained from an isopropylation reaction mixture and having the composition shown in Table 8 was distilled using a batch type distillation tower (inside diameter: 20 mm, height: 1800 mm) packed with a Mcmahon packing under a pressure of 50 mmHg with a reflux ratio of 20. As a result, a distillate (about 0.85 liter) free of 1,3- and 1,7-isomers having the composition shown in Table 9 was obtained.

TABLE 8

| Composition of Diisopropylnaphthalene | Content (% by weight) | Boiling Point (°C.) |
|---|---|---|
| 1,3-isomer | 18.6 | 309 |
| 1,7-isomer | 16.3 | 309 |
| 1,5-isomer | 3.4 | 311 |
| 1,4-isomer | 7.6 | 315 |
| 2,7-isomer | 17.2 | 317 |
| 1,6-isomer | 14.3 | 318 |
| 2,3-isomer | 4.5 | 318 |
| 2,6-isomer | 17.0 | 319 |
| others | 1.1 | — |

TABLE 9

(Distillate)

| Component | Content (% by weight) |
|---|---|
| 1,5-isomer | 1.2 |
| 1,4-isomer | 6.7 |
| 2,7-isomer | 27.5 |
| 1,6-isomer | 25.4 |
| 2,3-isomer | 7.9 |
| 2,6-isomer | 30.2 |
| others | 1.1 |

(b) Separation of 2,7-isomer by Adsorption:

About 10 g of a sodium-type Y-zeolite ($SiO_2/Al_2O_3$ molar ratio: 4.6, particle size: 40–80 mesh) were mixed with about 100 g of a 0.5 mol/liter aqueous solution of a metal chloride and the mixture was allowed to stand at 90°–100° C. for 2 hours for effecting ion-exchange with the metal. After filtration, the precipitate was mixed again with the above aqueous solution and the mixture was heat-treated in the same manner. The above procedures were repeated once more and the precipitate was dried and calcined at 400° C. for 3 hours to obtain an absorbent ion-exchanged with K (Absorbent No. 1) or Na (Absorbent No. 2).

Into a 30 cc autoclave, about 4 g of the absorbent, about 6.5 g of the above distillate having the composition shown in Table 9 and about 1.5 g of diethylbenzene (desorbent material) were added and the mixture was stirred for 120 minutes at a constant temperature. The resulting mixture was filtered. The absorbent was washed with isooctane and then subjected to extraction with toluene by means of a Soxhlet extractor. The filtrate and the extracted material were each analyzed by gas chromatography, from the results of which relative separation factors (2,7/i) were calculated. The results are shown in Table 10.

TABLE 10

| Absorbent | Ion Exchanged Metal | Relative Separation Factor β | | | | |
|---|---|---|---|---|---|---|
| | | (2,7/1,5) | (2,7/1,4) | (2,7/1,6) | (2,7/2,3) | (2,7/2,6) |
| No. 1 | K | 2.0 | 3.6 | 5.6 | 2.8 | 11.1 |
| No. 2 | Na | 2.0 | 9.6 | 3.3 | 2.0 | 1.3 |

(c) Separation of 2,6-isomer:

About 100 g of an isomeric mixture which had been obtained by the above distillation (a) and extraction (b) treatment and having the composition shown in Table 11 were mixed with about 30 g of n-hexane and the mixture was cooled to 0° C. to precipitate crystals. Filtration gave about 30 g of 2,6-isomer having a purity of 98.1%.

TABLE 11

| Component | Content (% by weight) |
|---|---|
| 1,5-isomer | 1.6 |
| 1,4-isomer | 9.2 |
| 1,6-isomer | 35.0 |
| 2,3-isomer | 11.0 |
| 2,6-isomer | 41.7 |
| others | 1.5 |

EXAMPLE 9

Using absorbent No. 1 shown in Example 8, a mixture of 20 parts by weight of the isomeric mixture having the composition shown in Table 9 and 80 parts by weight of a desorbent material shown in Table 12 was subjected to an extraction treatment (b) as described in Example 8, thereby to obtain relative separation factors shown in Table 12.

TABLE 12

| Desorbent material | Relative Separation Factor β | | | | | |
|---|---|---|---|---|---|---|
| | (2,7/1.5) | (2,7/1,4) | (2,7/1,6) | (2,7/2,3) | (2,7/2,6) | (2,7/D) |
| PDPB *1 | 4.2 | 8.5 | 18.5 | 2.5 | 28.5 | 12.8 |
| DB *2 | 2.0 | 3.6 | 5.6 | 2.8 | 11.1 | 1.4 |
| p-Cymene | 6.3 | 7.5 | 6.3 | 2.0 | 12.5 | 1.3 |
| Ethylbenzene | 5.6 | 20.1 | 4.3 | 1.9 | 12.2 | 6.3 |
| Toluene | 7.0 | 20.0 | 3.0 | 1.1 | 10.0 | 15.0 |

*1 p-Diisopropylbenzene
*2 Diethylbenzene

EXAMPLE 10

The isomeric mixture having the composition shown in Table 9 was subjected to an adsorption and desorption separation treatment for the removal of 2,7-isomer using a simulated, countercurrent moving bed system as shown in FIG. 1. Absorbent No. 1 (K-type Y-zeolite) was packed in 16 column chambers No. 101–116 (each inside volume: 70 ml). In the first step, the isomeric mixture was fed through the line 119, a desorbent material (diethylbenzene) through the line 117, while simultaneously discharging an extract through the line 118 and a raffinate through the line 120. The points of the feeding and discharging were shifted downward from one chamber to the adjacent downstream chamber with a predetermined interval so that the simulated displacing speed (S) of the absorbent was 18 cc/hour. The above procedure was carried out in various conditions (various feed rates and discharge rates) as shown in Table 13. The purity and recovery rate of 2,7-isomer are shown in Table 13.

TABLE 13

| Experiment No. | 1 | 2 | 3 | 4 | 5 | 6 |
|---|---|---|---|---|---|---|
| Desorbent material feed rate (cc/hr) | 247 | 130 | 232 | 312 | 293 | 409 |
| Extract discharge rate (cc/hr) | 131 | 24 | 246 | 188 | 155 | 246 |
| Isomeric mixture feed rate (cc/hr) | 57 | 41 | 90 | 148 | 33 | 33 |
| Raffinate discharge rate (cc/hr) | 173 | 147 | 76 | 272 | 171 | 196 |
| Liquid flow rate (cc/hr) | | | | | | |
| L(I) in desorbing zone | 998 | 883 | 982 | 1063 | 1145 | 982 |
| L(II) in concentrating zone | 867 | 859 | 736 | 875 | 990 | 736 |
| L(III) in adsorption zone | 924 | 900 | 826 | 1023 | 1023 | 769 |
| L(IV) in recovery zone | 751 | 753 | 750 | 751 | 852 | 573 |
| L(I)/S(I) | 1.22 | 1.08 | 1.20 | 1.30 | 1.40 | 1.20 |
| L(II)/S(II) | 1.06 | 1.05 | 0.90 | 1.07 | 1.21 | 0.90 |
| L(III)/S(III) | 1.13 | 1.10 | 1.01 | 1.25 | 1.25 | 0.94 |

TABLE 13-continued

| Experiment No. | 1 | 2 | 3 | 4 | 5 | 6 |
|---|---|---|---|---|---|---|
| L(IV)/S(IV) | 0.92 | 0.92 | 0.92 | 0.92 | 1.10 | 0.70 |
| Purity of 2,7-isomer (wt. %) | 99.2 | 98.1 | 53.1 | 98.0 | 35.1 | 32.1 |
| Recovery rate of 2,7-isomer (wt. %) | 95.7 | 65.1 | 95.3 | 42.1 | 64.2 | 98.0 |

In Experiment No. 2, in which L(I)/S(I) is excessively small, the 2,7-isomer is carried by the absorbent and is recirculated into the raffinate, so that the recovery rate thereof is decreased. In Experiment No. 3, in which L(II)/S(II) is excessively small, other isomers than the 2,7-isomer contaminate the extract so that the purity of the 2,7-isomer is reduced. Since, in Experiment No. 4, L(III)/S(III) is excessively large, the 2,7-isomer enters the raffinate flow to reduce the recovery rate. Too large an L(IV)/S(IV) in Experiment No. 5 causes other isomers than the 2,7-isomer contaminate the recovered desorbent material and, therefore, the extract. This lowers the purity of the 2,7-isomer product. In Experiment No. 6, on the other hand, the L(IV)/S(IV) is so small that other isomers than 2,7-isomer contaminate the extract to cause reduction of the purity of the 2,7-isomer product.

EXAMPLE 11

The isomeric mixture having the composition shown in Table 8 was subjected to an adsorption treatment in the same manner as that in Example 8 using the absorbent No. 1 (K-Y-zeolite). The relative separation factors were as shown in Table 14.

TABLE 14

| | Relative Separation Factor $\beta$ | | | | | | |
|---|---|---|---|---|---|---|---|
| Absorbent | (2,7/ 1,3) | (2,7/ 1,7) | (2,7/ 1,5) | (2,7/ 1,4) | (2,7/ 1,6) | (2,7/ 2,3) | (2,7/ 2,6) |
| No. 1 | 21.0 | 0.8 | 2.3 | 9.4 | 10.3 | 5.4 | 19.3 |

The above results show that 1,7-isomer can be separated together with the 2,7-isomer by adsorption. Since there exists a difference of 8° C. in boiling point between them (see Table 8), they can be separated from each other by distillation.

It was confirmed that when the isomeric mixture of Table 16 from which 2,7- and 1,7-isomers had been removed by adsorption as above was subjected to precipitation in the same manner as that in Example 8, the 2,6-isomer was able to be separated as crystals with a high purity.

EXAMPLE 12

The raffinate obtained in Example 10, Experiment No. 1 was distilled to remove the desorbent material, thereby to obtain a mixture having the composition shown in Table 15.

TABLE 15

| Component | Content (% by weight) |
|---|---|
| 1,5-isomer | 1.5 |
| 1,4-isomer | 9.1 |
| 2,7-isomer | 1.8 |
| 1,6-isomer | 34.4 |
| 2,3-isomer | 10.7 |
| 2,6-isomer | 41.0 |
| others | 1.5 |

The above mixture was then subjected to an adsorption and desorption separation treatment for the removal of 2,6-isomer using a simulated, countercurrent moving bed system as shown in FIG. 1. Absorbent No. 2 (Na-type Y-zeolite) shown in Table 10 was packed in 16 column chambers No. 101–116 (each inside volume: 70 ml). In the first stage, the isomeric mixture was fed at a feed rate of 25 ml/hr through the line 119, a desorbent material (diethylbenzene) at a feed rate of 80 ml/hr through the line 117, while simultaneously discharging an extract through the line 118 at a rate of 70 ml/hr and a raffinate through the line 120 at a rate of 35 ml. The points of the feeding and discharging were shifted downward from one chamber to the adjacent downstream chamber with an interval of 480 seconds. The 2,6-isomer was recovered as an extract with a purity of 99 wt % (desorbent free basis) and recovery rate of 90 wt %.

EXAMPLE 13

About 100 g of the isomeric mixture having the composition shown in Table 15 was mixed with about 30 g of n-heptane and the mixture was cooled at 0° C. for crystallization. About 25 g of the 2,6-isomer was obtained as crystals with a purity of 97.9 wt %.

EXAMPLE 14

The isomeric mixture (5.3 g) having the composition shown in Table 15 was mixed with 74.3 g of methanol and 18.9 g of thiourea and the mixture was stirred at 60° C. for 30 minutes. The resulting mixture was allowed to stand and to be gradually cooled to room temperature and then kept at $-5°$ C. for 18 hours. As a consequence, there was obtained a urea adduct. This adduct was filtered and washed with methyl ether and then decomposed with distilled water. Extraction of the decomposed mixture with benzene gave 2,6-isomer with a purity of 95.3 wt % and a recovery rate of 81.6%.

EXAMPLE 15

The 1,3- and 1,7-isomers-free isomeric mixture having the composition shown in Table 16 was subjected to an adsorption and desorption separation treatment for the removal of 2,7-isomer using a simulated, countercurrent moving bed system as shown in FIG. 1.

TABLE 16

| Component | Content (% by weight) |
|---|---|
| 1,5-isomer | 0.3 |
| 1,4-isomer | 0.3 |
| 2,7-isomer | 40.6 |
| 1,6-isomer | 8.3 |
| 2,3-isomer | 0.5 |
| 2,6-isomer | 48.7 |
| others | 1.3 |

Absorbent No. 1 (K-type Y-zeolite) shown in Table 10 was packed in 16 column chambers No. 101–116 (each inside volume: 70 ml). In the first stage, the isomeric mixture was fed at a feed rate of 30 ml/hr through the line 119, a desorbent material (diethylbenzene) at a feed rate of 113 ml/hr through the line 117, while simultaneously discharging an extract through the line 118 at a rate of 45 ml/hr and a raffinate through the line 120 at a rate of 98 ml. The points of the feeding and discharging were shifted downward from one chamber to the adjacent downstream chamber with an interval of 370 seconds. The 2,7-isomer was recovered as an extract with a purity of 99.5 wt % (desorbent free basis) and recovery rate of 99.1 wt %.

The thus obtained raffinate was distilled to remove the desorbent material and 100 g of the resulting isomeric mixture were cooled in the same manner as that in Example 8 to obtain about 70 g of 2,6-isomer crystals with a purity of 98.7 wt %.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A method of separating 2,6-diisopropylnaphthalene from a mixture containing 2,6-diisopropylnaphthalene and structural isomers thereof, including the 1,7-isomer and the 2,7-isomer, comprising the steps of:
   (a) contacting said mixture with a first zeolite absorbent to selectively adsorb the 1,7- and 2,7-isomers and desorbing said isomers from said first zeolite to obtain a first extract containing the 1,7- and 2,7-isomers and a first raffinate containing non-sorbed isomers including the 2,6-isomer; and
   (b) contacting said first raffinate with a second zeolite to adsorb the 2,6-isomer and desorbing said 2,6-isomer from said second zeolite to obtain a second extract containing the 2,6-isomer and a second raffinate containing non-sorbed isomers.

2. A method as claimed in claim 1, wherein each of said first and second zeolite absorbents has a $SiO_2/Al_2O_3$ molar ratio of 2–6.

3. A method as claimed in claim 1, wherein said first zeolite absorbent is a zeolite having at least 80 mole % of its exchangeable cations ion-exchanged with at least one cation selected from the group consisting of Li, Na, K, Ba and Pb ions and said second zeolite absorbent is a zeolite having at least 80 mole % of its exchangeable cations ion-exchanged with at least one cation selected from the group consisting of Na, Pb and Ba.

4. A method as claimed in claim 3, wherein each of said first and second zeolite absorbents has a moisture content of 5% by weight or less.

5. A method as claimed in claim 1, wherein the selective adsorption and desorption treatment in each of steps (a) and (b) is performed at a temperature of about 80°–200° C. and a pressure so that said mixture is present in a liquid state.

6. A method as claimed in claim 1, further comprising subjecting said first extract to distillation treatment to separate the 1,7- and 2,7-isomers from each other.

7. A method as claimed in claim 1, wherein step (a) includes:
   (i) contacting said mixture with said first zeolite absorbent contained in an adsorption zone and maintained at adsorption conditions to effect selective adsorption of 2,7-isomer contained in said mixture;
   (ii) withdrawing from the adsorption zone said first raffinate;
   (iii) contacting said first zeolite absorbent carrying the adsorbed 2,7-isomer and maintained at desorption conditions with a desorbent material to effect removal of the 2,7-isomer therefrom; and
   (iv) withdrawing from said zeolite absorbent said first extract containing the removed 2,7-isomer.

8. A process as claimed in claim 7, wherein said desorbent material is an alkylbenzene of the formula:

$(R')_n$-Ph-R wherein Ph represents a benzene nucleus, R and R' represent independently from each other a methyl, an ethyl, an n-propyl or an isopropyl, and n is an integer of 0 or 1.

9. A process as claimed in claim 1, wherein step (a) includes the steps of:
   providing a simulated countercurrent moving bed system which includes a fixed bed of a said first zeolite absorbent containing at least four serially interconnected zones having fluid flow connecting means between adjacent zones and between the outlet of the last zone and the inlet of the first zone in the series, to thereby provide cyclic, fluid flow in said system;
   introducing said mixture into one, sorbing zone of said fixed bed to selectively sorb the 2,7-isomer contained in said mixture;
   introducing a desorbent material to another, desorbing zone of said fixed bed to remove the sorbed 2,7-isomer, said desorbing zone being positioned upstream of said sorbing zone such that an intermediate, concentrating zone is defined between said sorbing and desorbing zones and that a recovering zone is defined downstream of said sorbing zone;
   substantially simultaneously withdrawing non-sorbed isomers from the fluid flow connecting means extending between said sorbing and recovering zones as said first raffinate;
   substantially simultaneously withdrawing the removed 2,7-isomer from the fluid flow connecting means extending between said desorbing and concentrating zones as said first extract; and
   periodically advancing downstream the point of introducing said mixture, while simultaneously and equally advancing the points of introducing the desorbent material and of withdrawing said first raffinate and said first extract.

10. A method as claimed in claim 1, wherein before step (a) said mixture is subjected to a distillation treatment to separate the 1,3- and 1,7-isomers therefrom, the resulting mixture from which the 1,3- and 1,7-isomers have been removed being subjected to step (a).

11. A process as claimed in claim 10, wherein step (a) includes:
   (i) contacting said resulting mixture with said first zeolite absorbent contained in an adsorption zone and maintained at adsorption conditions to effect selective adsorption of the 2,7-isomer contained in said mixture;
   (ii) withdrawing from the adsorption zone said first raffinate;
   (iii) contacting said first zeolite absorbent carrying the adsorbed 2,7-isomer and maintained at desorption conditions with a desorbent material to effect removal of the 2,7-isomer therefrom; and
   withdrawing the removed 2,7-isomer from said zeolite
   (iv) absorbent as said first extract containing the removed 2,7-isomer.

12. A process as claimed in claim 11, wherein said first zeolite absorbent is an Y zeolite having at least a portion of its exchangeable cations ion-exchanged with potassium ions.

13. A process as claimed in claim 11, wherein said desorbent material is an alkylbenzene of the formula:

(R')$_n$-Ph-R wherein Ph represents a benzene nucleus, R and R' represent independently from each other a methyl, an ethyl, an n-propyl or an isopropyl, and n is an integer of 0 or 1.

14. A process as claimed in claim 8, wherein step (a) includes the steps of:

providing a simulated countercurrent moving bed system which includes a fixed bed of said first zeolite absorbent containing at least four serially interconnected zones having fluid flow connecting means between adjacent zones and between the outlet of the last zone and the inlet of the first zone in the series, to thereby provide cyclic, fluid flow in said system;

introducing said resulting mixture into one, sorbing zone of said fixed bed to selectively sorb the 2,7-isomer contained in said resulting mixture;

introducing a desorbent material to another, desorbing zone of said fixed bed to remove the sorbed 2,7-isomer, said desorbing zone being positioned upstream of said sorbing zone such that an intermediate, concentrating zone is defined between said sorbing and desorbing zones and that a recovering zone is defined downstream of said sorbing zone;

substantially simultaneously withdrawing the non-sorbed isomers from the fluid flow connecting means extending between said sorbing and recovering zones as said first raffinate;

substantially simultaneously withdrawing the removed 2,7-isomer from the fluid flow connecting means extending between said desorbing and concentrating zones as said first extract; and periodically advancing downstream the point of introducing said resulting mixture, while simultaneously and equally advancing the points of introducing the desorbent material and of withdrawing said first raffinate and said first extract, said desorbing, concentrating, sorbing and recovering zones being operated under conditions satisfying the following formulas:

| | |
|---|---|
| desorbing zone: | L(I)/S(I) > 0.2 + L(IV)/S(I) |
| concentrating zone: | L(II)/S(II) > 0.1 + L(IV)/S(II) |
| sorbing zone: | L(III)/S(III) < 0.3 + L(IV)/S(III) |
| recovering zone: | 0.8 < L(IV)/S(IV) < 1.0 | wherein L(I) through L(IV) represent the flow rates, in terms of cc/hour, of liquids flowing through said desorbing zone, concentrating zone, sorbing zone and recovering zone, respectively, and S(I) through S(IV) represent the simulate moving rates, in terms of cc/hour, of said first zeolite absorbent through said desorbing zone, concentrating zone, sorbing zone and recovering zone, respectively.

15. A method of separating 2,7-diisopropylnaphthalene from a mixture containing 2,7-diisopropylnaphthalene and structural isomers thereof, including the 1,3- and 1,7-isomers, comprising the steps of:

(a) distilling said mixture to obtain a fraction substantially free of the 1,3- and 1,7-isomers; and (b) contacting said first fraction with a zeolite to selectively absorb the 2,7-isomer and desorbing said 2,7-isomer from said zeolite to obtain a first extract containing the 2,7-isomer and a first raffinate containing non-sorbed isomers.

16. A process as claimed in claim 15, wherein said zeolite absorbent is a Y zeolite having at least a portion of its exchangeable cations ion-exchanged with potassium ions.

* * * * *

UNITED STATES PATENT AND TRADEMARK OFFICE
CERTIFICATE OF CORRECTION

PATENT NO. : 4,992,622

DATED : February 12, 1991

INVENTOR(S) : SHIROTO et al.

It is certified that error appears in the above-identified patent and that said Letters Patent is hereby corrected as shown below:

Col. 1, line 55, "form" should read --from--.

Col. 9, line 30, "ß(2,6i)" should read --ß(2,6/i)--.

Col. 10, line 54, "cm2" should read --$cm^2$--.

Col. 16, line 59, before "withdrawing" insert --(iv)--;

line 61, before "absorbent" delete "(iv)".

Col. 17, line 8, "8" should read --7--.

Signed and Sealed this

Eleventh Day of August, 1992

Attest:

DOUGLAS B. COMER

Attesting Officer

Acting Commissioner of Patents and Trademarks